(12) United States Patent
Lindner et al.

(10) Patent No.: US 9,821,341 B2
(45) Date of Patent: Nov. 21, 2017

(54) APPARATUS FOR GENERATING MECHANICAL OSCILLATIONS AND A METHOD FOR DETERMINING THE RESONANCE FREQUENCY OF SUCH APPARATUS

(71) Applicant: Rolls-Royce Mechanical Test Operations Centre GmbH, Blankenfelde-Mahlow (DE)

(72) Inventors: Maik Lindner, Berlin (DE); Jan Schnitzler, Berlin (DE)

(73) Assignee: Rolls-Royce Deutschland Ltd & Co KG, Blankenfelde-Mahlow (DE)

( * ) Notice: Subject to any disclaimer, the term of this patent is extended or adjusted under 35 U.S.C. 154(b) by 520 days.

(21) Appl. No.: 14/516,046

(22) Filed: Oct. 16, 2014

(65) Prior Publication Data
US 2015/0130324 A1 May 14, 2015

(30) Foreign Application Priority Data
Oct. 17, 2013 (DE) .................... 10 2013 221 096

(51) Int. Cl.
| | | |
|---|---|---|
| *H01L 41/09* | (2006.01) | |
| *B06B 1/06* | (2006.01) | |
| *B06B 1/02* | (2006.01) | |
| *G01M 5/00* | (2006.01) | |
| *G01N 3/38* | (2006.01) | |

(52) U.S. Cl.
CPC .......... *B06B 1/0614* (2013.01); *B06B 1/0269* (2013.01); *B06B 1/0611* (2013.01); *G01M 5/0016* (2013.01); *G01M 5/0066* (2013.01); *G01N 3/38* (2013.01)

(58) Field of Classification Search
CPC ....... A61B 8/12; A61B 8/4483; B06B 1/0622; B06B 1/0688; H01L 41/047; H01L 41/0472; H01L 41/0825; H01L 41/093; H01L 41/29; H01L 41/31; H01L 41/1132
USPC ........................................ 310/334, 336, 338
See application file for complete search history.

(56) References Cited

U.S. PATENT DOCUMENTS

| | | | |
|---|---|---|---|
| 3,309,654 A | * | 3/1967 | Miller .................. B06B 1/0618 367/158 |
| 4,491,759 A | | 1/1985 | Kunz et al. |
| 5,553,501 A | | 9/1996 | Gaddis et al. |

(Continued)

FOREIGN PATENT DOCUMENTS

| | | | | |
|---|---|---|---|---|
| AT | 399052 B | * | 7/1994 | ............... G01N 9/00 |
| AT | 399052 | | 3/1995 | |

(Continued)

OTHER PUBLICATIONS

European Search Report dated Oct. 30, 2015 from counterpart European App No. 14189356.0.

(Continued)

*Primary Examiner* — Thomas Dougherty
(74) *Attorney, Agent, or Firm* — Shuttleworth & Ingersoll, PLC; Timothy Klima

(57) ABSTRACT

A device for generating mechanical oscillations is provided. The device has a first mass, a second mass, and a piezoelectric excitation system mechanically coupling the first mass and the second mass to one another, with the piezoelectric excitation system having a stiffness. The piezoelectric excitation system is designed such that its stiffness is settable.

13 Claims, 9 Drawing Sheets

(56) References Cited

U.S. PATENT DOCUMENTS

| | | | |
|---|---|---|---|
| 6,023,980 A | | 2/2000 | Owen et al. |
| 6,109,109 A | * | 8/2000 | Brown ............... G01N 29/2437 367/159 |
| 6,813,960 B1 | | 11/2004 | Owen et al. |
| 7,019,439 B2 | * | 3/2006 | DeCastro ............. B06B 1/0618 310/322 |
| 7,556,677 B2 | | 7/2009 | Cranford et al. |
| 2010/0288038 A1 | * | 11/2010 | Wallaschek ............. G01N 3/38 73/121 |

FOREIGN PATENT DOCUMENTS

| | | | | |
|---|---|---|---|---|
| DE | 2939923 A1 | 4/1981 | | |
| DE | 10114672 A1 | 9/2002 | | |
| DE | 102004041061 | 3/2006 | | |
| EP | 0758455 A1 | 2/1997 | | |
| EP | 2503317 | 6/2013 | | |
| GB | 2060179 | 4/1981 | | |
| GB | 2060179 A | 4/1981 | | |
| WO | WO9530912 A1 | 11/1995 | | |
| WO | WO-98/37400 | * | 8/1998 | ............... G01N 3/32 |

OTHER PUBLICATIONS

German Search Report dated Feb. 28, 2014 from counterpart German App No. 10 2013 221 096.5.

* cited by examiner

|   | Description | Value | Unit |
|---|---|---|---|
| 1 | Test frequency | 2100 | [Hz] |
| 2 | Exciter - natural frequency | 2130,8 | [Hz] |
|   | Mass properties | | |
| 3 | Total mass | 4,5 | kg |
|   | Yoke | 4,5 | kg |
|   | Additional mass | 0,00 | kg |
| 4 | Total centrifugal mass | 17,30 | kg |
|   | Mass | 17,2 | kg |
|   | Additional mass | 0,10 | kg |
|   | Geometry (piezo) | | |
| 5 | Inside diameter | 20 | [mm] |
| 6 | Outside diameter | 50 | [mm] |
| 7 | Thickness | 6 | [mm] |
| 8 | Number (even) | 20 | [-] |
| 9 | Piezo stack (1, 2, 3,…) | 1 | [-] |
|   | Length of stack | 13,47 | [cm] |
| 10 | Correction factor | 1,7 | [-] |

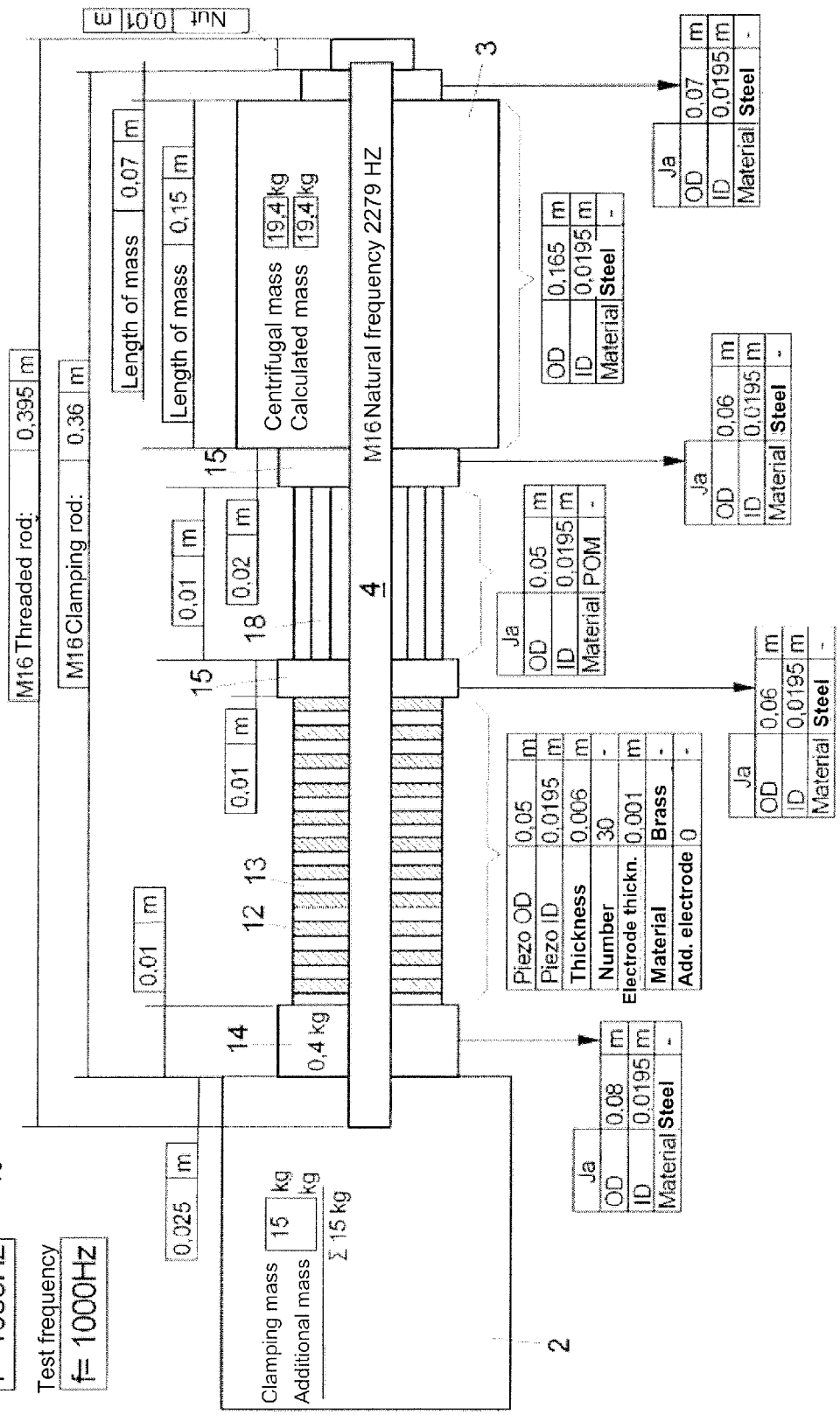

APPARATUS FOR GENERATING MECHANICAL OSCILLATIONS AND A METHOD FOR DETERMINING THE RESONANCE FREQUENCY OF SUCH APPARATUS

CROSS-REFERENCE TO RELATED APPLICATION

This application claims priority to German Patent Application DE102013221096.5 filed Oct. 17, 2013, the entirety of which is incorporated by reference herein.

BACKGROUND

This invention relates to a device for generating mechanical oscillations and to a method for calculating the resonance frequency of such a device.

Assessment of the service life of test objects by fatigue tests is known. To do so, the test object is excited with a resonance frequency of the test object. Excitation is achieved by means of a device for generating mechanical oscillations or by means of an oscillator including a piezoelectric excitation system and two masses coupled by it. The test objects on which fatigue tests are conducted are for example engine components, e.g. stator vanes or rotor blades of a turbine.

To ensure that a test object is excited in a resonance frequency, it is required that the oscillator also oscillates in the resonance frequency of the test object. To do so, the natural frequency of the oscillator must match that of the test object. Additionally, the AC voltage signal applied to the oscillator must have this frequency.

Piezoelectric excitation systems are based on the inverse piezo effect and are used, among others, in the field of fatigue tests. The general setup includes two masses bolted to one another as well as piezo elements arranged between them, said masses being subjected to a mechanical pretension. One of the masses is used as the yoke in which the test object is clamped. The natural frequency of a piezoelectric excitation system of this type is dependent on the piezo material of the piezo element and on the masses involved. The natural frequency is thus determined by the design constraints of the piezoelectric excitation system. To allow the generation of differing resonance frequencies for differing test objects, a plurality of piezoelectric excitation systems each having a differing natural frequency must be kept available.

It must be regarded as a disadvantage that the known piezoelectric excitation systems can each serve only one natural frequency or a narrow band of natural frequencies, and that a plurality of these piezoelectric excitation systems must be kept available in order to cater for differing resonance frequencies. There is a need for a device to generate mechanical oscillations which can be set in respect of its natural frequency and accordingly used to generate resonances of test objects in a wide frequency range.

SUMMARY

An object underlying the present invention is to provide a device for generating mechanical oscillations, where the natural frequency is variable and hence adjustable to the resonance frequency of a test object.

It must also be attempted, in a device for generating mechanical oscillations where the natural frequency can be set, to determine the setting of a desired natural frequency not by trial-and-error alteration of parameters, but by analytic prognoses in the framework of a mathematical model, so that a desired natural frequency of the device can be set without any loss of time.

Another object underlying the present invention therefore is to provide a method for calculating the resonance frequency of such a device for generating mechanical oscillations.

It is a particular object of the present invention to provide solution to the above problems by a device having the features as described herein and a method having the features as described herein.

The device in accordance with the invention provides that the piezoelectric excitation system, by which a first mass and a second mass of the device are mechanically coupled to one another, is designed such that its stiffness can be set. The first mass and the second mass are in this case not an integral part of the piezoelectric excitation system with settable stiffness.

The solution in accordance with the invention exploits the fact that a piezoelectric excitation system mechanically coupling two masses to one another has by its nature a certain stiffness. The solution in accordance with the invention is based on the knowledge that this stiffness co-determines the natural frequency of the device formed by the two masses and the piezoelectric excitation system, and that the natural frequency can be set by changing the stiffness. In particular, the extensional stiffness of the piezoelectric excitation system co-determines the natural frequency of the device in the case of oscillations applied in the longitudinal direction of the piezoelectric excitation system.

In the mathematical model, the overall system can be described as a two-mass oscillator, where the two masses are coupled to one another by a spring and where the spring constant matches the stiffness constant of the piezoelectric excitation system. By setting the stiffness of the piezoelectric excitation system, the spring constant of the spring coupling the two masses to one another is changed in the mathematical model, thus also changing the natural frequency of the overall system.

The principle is that a reduction in the stiffness of the piezoelectric excitation system leads to a drop in the natural frequency of the device, and an increase in the stiffness of the piezoelectric excitation system leads to an increase in the natural frequency of the device.

According to an embodiment of the invention, the piezoelectric excitation system has a plurality of piezoelectric wafers in contact with one another and forming a stack. It is provided that for setting its stiffness, the number and/or size of the piezoelectric wafers in the piezoelectric excitation system are variably settable. Parameters defining the size of a piezoelectric wafer are for example the thickness and the diameter or the cross-sectional area of the wafers. According to this variant of the invention, the stiffness of the piezoelectric excitation system can be variably set using the number and/or size of the piezoelectric wafers. If for example the number of wafers of the excitation system is increased, the stiffness of the excitation system is reduced, leading to a reduced natural frequency of the device.

To ensure that the number and/or size of the piezoelectric wafers in the piezoelectric excitation system are variably settable, it is provided according to a design variant of the invention that the piezoelectric wafers have holes, so that they can be slid or screwed onto a connecting rod that connects the first mass and the second mass to one another. It can be provided here that the connecting rod is designed as a threaded rod and is bolted at its ends to the two masses of the oscillation-generating device. In the area between the two masses, the piezoelectric wafers are screwed or slid onto the threaded rod and so form a stack of a defined length. In this way, the number and/or size of the piezoelectric wafers of the stack can be varied, with the stack height being identical or changed.

According to a further embodiment of the invention, the first mass is designed as a yoke into which a test object can be inserted and clamped. The second mass represents a centrifugal mass of the system. For example, a stator vane or rotor blade of an engine component to be tested in respect of its fatigue properties is clamped in the yoke forming the first mass.

To set the natural frequency of the device in accordance with the invention, it can be provided that additionally to the stiffness of the piezoelectric excitation system, further parameters of the device are changed and varied to obtain a desired natural frequency.

A further possibility for changing the natural frequency of the device lies in the settability of the first and/or second mass. Since the natural frequency depends on the two masses coupled to one another by the piezoelectric excitation system, the natural frequency can be influenced by the selection of said masses. It can for example be provided here that the respective masses are designed to be settable by the bolting on of additional weights. It can also be provided that the first mass and/or the second mass are kept available with differing weights and can each be substituted in simple manner, for example by providing bolted connections to the piezoelectric excitation system that connects them.

According to a further variant of the invention, the natural frequency of the device in accordance with the invention can be changed in that the mass ratio between the first mass and the second mass can be set. The greater the mass difference between the two masses, the wider the frequency band generated in the resonance range. Accordingly, the energy transmission in the resonance range is comparatively low. The smaller the mass difference is, by contrast, the narrower the frequency band in the resonance range. In this case, there is a comparatively large energy transmission in the resonance range. Here, a larger energy transmission or acceleration is provided in the relatively smaller mass.

According to a further variant of the invention, the natural frequency of the device in accordance with the invention can be changed in that the material of the piezoelectric wafers in the piezoelectric excitation system can be set. The intensity of the inverse piezoelectric effect is determined by the piezoelectric material of the wafers, so that the natural frequency can be set by the selection of the material. For example, piezoelectric wafers made of differing materials are kept available for this purpose, and can be substituted in simple manner by sliding them onto a threaded rod. In this variant of the invention, the natural frequency is also changed by a settability of the stiffness of the piezoelectric excitation system, since the material of the piezoelectric wafers co-determines the stiffness of the piezoelectric excitation system.

It is pointed out in general that the mechanical pretensioning of the individual components of the device is selected such that a maximum coupling and energy transmission between the first mass and the second mass is achieved by the piezoelectric excitation system. The pretensioning can, for example, be determined by means of bolts and/or nuts in a bolted connection between the two masses and the piezoelectric excitation system.

In further embodiments of the invention, further parameters of the device in accordance with the invention can be set in order to change the natural frequency of the device.

For example, it can be provided that in addition the level of the operating voltage to which the piezoelectric excitation system is subjected can be set. Experimental tests have shown that the resonance frequency decreases slightly when the operating voltage is increased.

According to a further embodiment of the invention, at least one of the two masses of the device in accordance with the invention is provided with more than one fastening means for fastening of the piezoelectric excitation system, with the piezoelectric excitation system being optionally fastenable to each of the fastening means. To that end, it can for example be provided that at least one of the masses has several flat mounting surfaces and a hole arranged in the centre of each one for receiving a threaded rod. In particular, it can be provided that these differing mounting surfaces are designed on the mass forming the yoke. By connecting the piezoelectric excitation system to the yoke at differing mounting surfaces, the angle at which force is introduced is altered in each case, so that the natural frequency of the device can be altered or another mode can be excited.

The present invention also relates to a method for setting the resonance frequency of a device for generating mechanical oscillations, said device having a first mass, a second mass and a piezoelectric excitation system mechanically connecting these masses to one another and having a settable stiffness. The method includes the following steps:
  recording of parameters defining the stiffness of the piezoelectric excitation system,
  calculation of the resonance frequency of the device using these parameters and the first and second mass,
  where the calculation of the resonance frequency is based on the movement equations of a two-mass oscillator.

The movement equations of a two-mass oscillator are here described by the movement equation:

$$\underline{M}\dot{x} + \underline{B}\dot{x} - \underline{K}x = \underline{f(t)}$$

where M indicates the mass matrix, B the damping matrix, K the stiffness matrix, x the movement direction of a mass and f the frequency.

In a simplified view that ignores any damping of the system and considers only a longitudinal movement direction of the two masses, the resonance frequency is obtained from the formula:

$$(f_2)_{1,2} = +/- \frac{1}{2\Pi} \sqrt{\frac{k(m_1 + m_2)}{m_1 m_2}}.$$

where $m_1$ indicates the first mass, $m_2$ the second mass, k the stiffness constant (i.e. the stiffness) of the overall system, and $(f_2)_{1,2}$ the resonance frequency.

The stiffness constant of the overall system is made up of the stiffness of the masses connected in series and of the components of the piezoelectric excitation system which is settable with regard to its stiffness.

In the event that the piezoelectric excitation system consists of a plurality of piezoelectric wafers which are fitted together with electrodes onto a threaded rod connecting the masses to be coupled (in the following also referred to as "piezo stack"), the stiffness constant of the overall system is made up of the stiffness of the masses connected in series and fitted onto the threaded rod, the stiffness of the electrodes, the stiffness of the piezoelectric wafers and the stiffness of the threaded rod connected in parallel. According to a design variant, the stiffness of the overall system is calculated according to the following formula:

$$k = \frac{1}{\sum_{i=1}^{n} \frac{1}{k_{m,i}} + \frac{1}{k_{Piezo}} + \frac{1}{k_{Elektrode}}} + k_{M16}$$

Here, $k_{m,i}$ indicates the stiffness constant of the $i^{th}$ mass $m_i$, $k_{piezo}$ the stiffness constant of the piezoelectric wafers, $k_{elektrode}$ the stiffness constant of the electrodes and $k_{M16}$ the stiffness constant of the threaded rod. The masses $m_i$ are in particular a centrifugal mass and, where necessary, further masses located on the threaded rod, such as the masses of additional plates.

The parameters determining the stiffness $k_{piezo}$ of the piezoelectric wafers are here, according to one embodiment, defined as the number, size (in particular diameter and thickness), shape and/or material of the piezoelectric wafers. In accordance with a design variant, the stiffness of the piezoelectric wafers is calculated according to the following formula:

$$k_{Piezo} = \frac{A}{S_{33}^E * d * n}$$

Here, $k_{piezo}$ is the stiffness constant of the piezoelectric wafers of the piezoelectric excitation system, n the number of the piezoelectric wafers, d the thickness of the piezoelectric wafers, A the surface of a piezoelectric wafer and $S^E_{33}$ the elasticity coefficient of the material of the piezoelectric wafers in their longitudinal direction. The compliance or elasticity coefficient $S^E_{33}$ is defined here as the ratio of the relative deformation S to the mechanical tension T.

The stiffness constant is thus obtained from the quotient of wafer area and the product of the three factors $S^E_{33}$, d and n. The stiffness constant has the unit kg*s$^{-2}$.

The stiffness constant of the electrodes of the piezoelectric excitation system is calculated according to the following formula:

$$k_{Elektrode} = \frac{E * A_{ers}}{L * n}$$

The stiffness constant of the respective masses fitted onto the threaded rod is calculated according to the following formula:

$$k_{m,i} = \frac{E * A_{ers}}{L}$$

Here, $k_{m,i}$ is the stiffness constant of the respective mass $m_i$, E the material-specific modulus of elasticity, $A_{ers}$ the substitute cross-sectional area, n the number of identical electrodes and L the mass length in the longitudinal direction. The stiffness constant $k_{elektrode}$ thus results from a quotient consisting of the product of the two factors E and $A_{ers}$ in the numerator, and of the product of the mass length L and the number n in the denominator. The stiffness constant $k_{m,i}$ thus results from a quotient consisting of the product of the two factors E and $A_{ers}$ in the numerator, and of the mass length L in the denominator. The stiffness constant has the unit kg*s$^{-2}$.

The substitute cross-sectional area $A_{ers}$ of the respective masses and electrodes is calculated, in the event that the latter have a cylindrical shape, according to the following formula as a function of the following case distinction:

if $D_a \leq d_w$, then:

$$A_{ers} = \frac{\pi}{4(D_a^2 - D_i^2)}$$

if $d_w \leq D_a \leq d_w + L$, then:

$$A_{ers} = \frac{\pi}{4}(d_w^2 - D_i^2) + \frac{\pi}{8}d_w(D_a - d_w)\left[\left(\sqrt[3]{\frac{L*d_w}{D_a^2}+1}\right)^2 - 1\right]$$

if $D_a > d_w + L$, then:

$$A_{ers} = \frac{\pi}{4}(d_w^2 - D_i^2) + \frac{\pi}{8}d_w * L\left[\left(\sqrt[3]{\frac{L*d_w}{(L+d_w)^2}+1}\right)^2 - 1\right]$$

Here, $D_a$ is the outside diameter of the respective mass m, $D_i$ the inside diameter of the respective mass m, L the mass length in the longitudinal direction and $d_w$ the outside diameter of the force-transmitting area of a mass or electrode. The substitute cross-sectional area $A_{ers}$ has the unit m$^2$.

The force-transmitting area is here in each case the smaller contact area between adjacent masses or electrodes. The substitute cross-sectional area represents a dimension for the force flow between two adjacent masses or electrodes.

The stiffness constant $k_{M16}$ of the threaded rod is calculated according to the following formula:

$$k_{M16} = \frac{E * A_S}{L}$$

Here, $k_{M16}$ is the stiffness constant of the threaded rod, E the material-specific modulus of elasticity, $A_s$ the tension cross-sectional area and L the length in the threaded rod.

As already set forth in respect of the device in accordance with the invention, the calculation method in accordance with the invention can take into account further parameters co-determining the natural frequency of the oscillator device.

In the event that the resonance frequency calculated by the method in accordance with the invention is unequal to a required resonance frequency, it can be provided that at least one parameter affecting the stiffness of the piezoelectric excitation system is reset to achieve a desired natural frequency. It can be provided here that a computer program performing the method submits proposals for a parameter selection leading to a desired natural frequency.

The invention also relates to a computer program with software code for performing the process steps as described herein, when the computer program is run on a computer.

BRIEF DESCRIPTION OF THE DRAWINGS

The present invention is described in the following with reference to the figures of the accompanying drawing, showing an exemplary embodiment.

FIG. 8 shows a further user interface of a computer program that calculates the resonance frequency of the device of FIG. 1 on the basis of system parameters.

DETAILED DESCRIPTION

Figure 1:
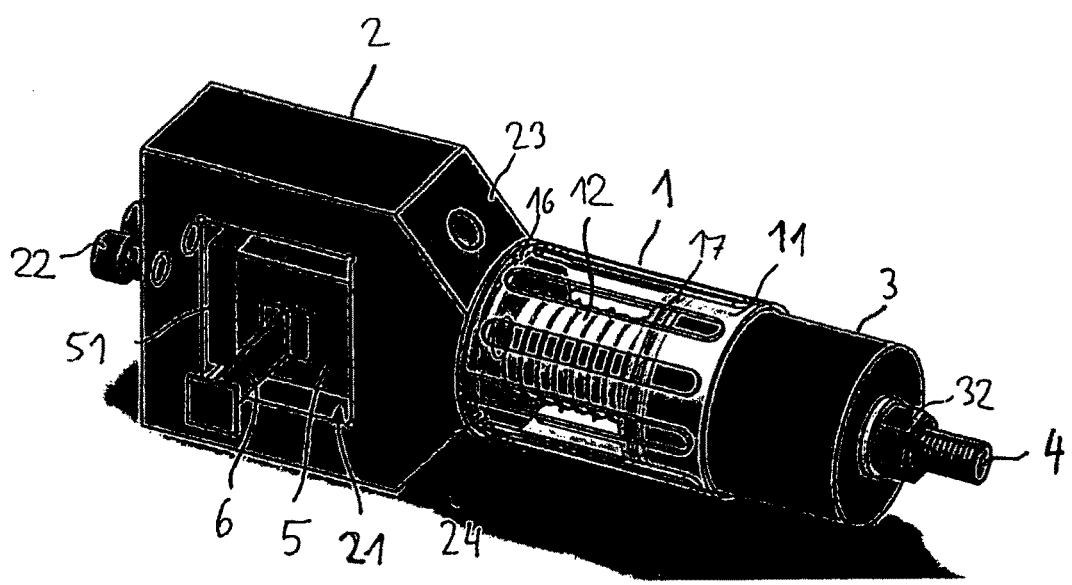
FIG. 1 shows a perspective view of an exemplary embodiment of a device in accordance with the present invention for generating mechanical oscillations.
Figure 2:
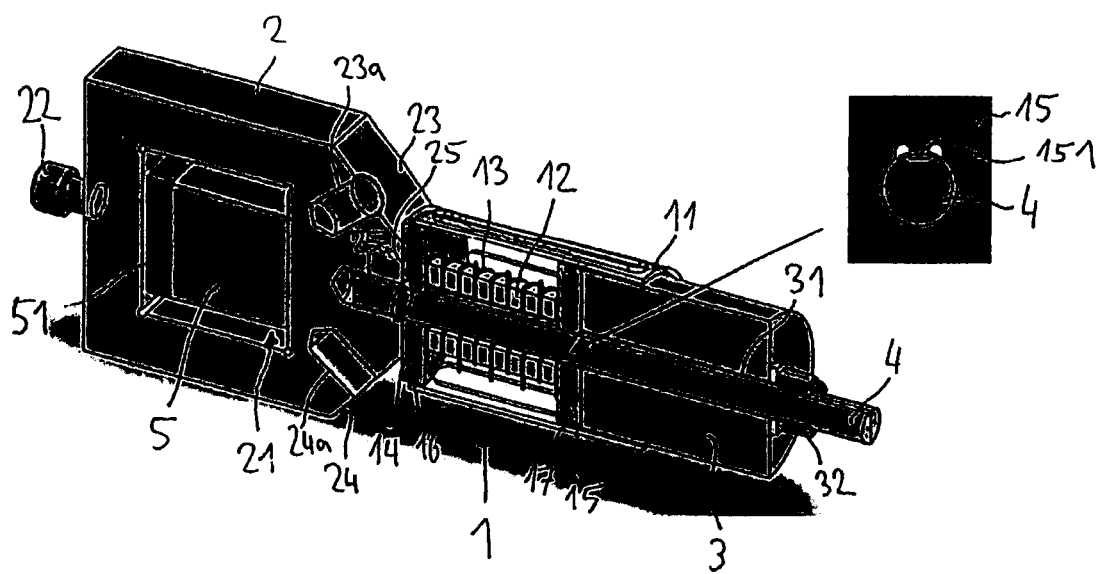
FIG. 2 shows a sectional view of the device of FIG. 1.

The FIGS. 1 and 2 show a device in accordance with the present invention for generating mechanical oscillations. The main components of the device are a first mass 2, a second mass 3 and a piezoelectric excitation system 1 mechanically coupling the two masses 2, 3.

The first mass 2 forms a yoke used for receiving and clamping a test object 6, in the present case a blade of an engine component. To do so, the yoke 2 has a recess 21 inside which is arranged a clamping block 5 into which the test object 6 is clamped by bolting it in place. It can be provided here that the clamping block 5 is rigidly arranged inside the recess 21 by means of an elastic element 51.

Bolts 22, which are used for example to fix the device to an adjacent structure, can furthermore be inserted into the clamping block 2 on the side facing away from the piezoelectric excitation system 1.

The yoke 2 furthermore includes three mounting surfaces 23, 24, 25 each provided in the centre with a hole 23a, 24a, 25a (for example a tapped hole), with the three mounting surfaces 23, 24, 25 being arranged at an angle of, for example, 40° to one another. The piezoelectric excitation system 1 can be bolted and coupled to any of these mounting surfaces 23, 24, 25.

The second mass 3 represents a centrifugal mass. It has a central hole 31 using which the second mass 3 is screwed or fitted onto a connecting rod, e.g. a threaded rod 4, passing through the second mass 3 and the piezoelectric excitation system 1 and connecting the two masses 2, 3 and the piezoelectric excitation system 1 to one another. In this way, the one end of the threaded rod 4 is screwed into the hole 25a of the mass 2. The masses 2, 3 are bolted to one another using the threaded rod 4 and pretensioned.

The piezoelectric excitation system 1 is located between the two masses 2, 3 and has a plurality of piezoelectric wafers 12 in contact with one another and forming a stack. An electrode 13 is provided between the piezoelectric wafers 12 in each case, for example made of brass and having a brazing point for an electrical connection. The electrodes 13 are electrically connected in parallel, so that the same voltage is applied to all electrodes 13. Additionally, the first and the last components of the stack are designed as an electrode 13. The stack of piezoelectric wafers 12 (also referred to as "piezo stack") is enclosed by a protective tube 11.

The piezoelectric wafers 12 and the electrodes 13 have a central hole and are concentrically positioned as one unit by the threaded rod 4, which is additionally electrically insulated by a silicone tube. In front of and behind the stack formed by the piezoelectric wafers 12 an additional plate 14, 15 is located which engages, as shown in the enlarged view in FIG. 2, with a tooth-like web 151 into the groove of the threaded rod 4. The additional plates 14, 15 prevent transmission of a torque onto the piezo elements 12 during pretensioning of the device.

Furthermore, the additional plates 14, 15 each have on their outer cylindrical surface a circumferential groove in which is fitted an O-ring 16, 17 respectively. The sealing rings 16, 17 are used to guide the protective tube 11 enclosing the area of the piezoelectric elements 12.

The protective tube 11 has oblong holes distributed along its circumference to allow compressed air to be blown onto the stack of piezoelectric wafers 12 in order to remove the heat being generated.

The mounting sequence is such that first the piezoelectric arrangement 1 is mounted and the threaded tube 4 is bolted inside the hole 25a of the yoke 2 (in any order). Then the second mass 3 behind the additional plate 15 is slid onto the threaded rod 4 and fixed by means of a final nut 32 and a washer. Mechanical pretensioning of the system is achieved by a torque-controlled tightening process. In other words, it is possible by tightening the nut 32 and/or turning the yoke 2 to set the mechanical pretensioning, i.e. the degree of mechanical coupling between the two masses 2, 3.

Not shown in the FIGS. 1 and 2 is an electrical connection via which an AC voltage is applied to the electrodes 13 for periodic generation of the inverse piezoelectric effect. Due to the inverse piezoelectric effect and the mechanical coupling of the mass 2 to the piezoelectric excitation system 1 and its coupling to the mass 3, the mass 2 or the yoke is subjected to oscillations that are transmitted via the clamping block 5 to the test object 6.

To achieve the resonance case, i.e. excitation of the test object 6 with one of its resonance frequencies, it is required that the device too and hence the yoke 2 oscillates with one of the resonance frequencies. This means that the natural frequency of the device consisting of the components 1, 2, 3 must match or approximately match the resonance frequency of the test object 6, as otherwise the supplied energy does not build up to the resonance case. Furthermore, it is required that the signal of the AC voltage with which the piezoelectric excitation system 1 is actuated also has or approximately has the desired resonance frequency.

The device in FIGS. 1 and 2 enables the natural frequency of the device to be set over a wide range without design changes, thereby ensuring that with a single device a wide range of resonance frequencies of test objects to be tested can be covered. For example, the device can be set over a frequency range between 0.3 and 35 kHz.

The settability of the frequency of the device in accordance with the invention is achieved in the exemplary embodiment considered by the option of setting the stiffness of the piezoelectric excitation system 1, in particular by variation of the piezoelectric wafers 12, and by the option of setting further parameters of the device.

In particular, it is possible, with the embodiment of the piezoelectric wafers 12 with holes in accordance with the invention, to vary the number and/or size and/or material of the wafers 12 and hence set the stiffness of the piezoelectric excitation system 1 and the natural frequency of the device. For example, the number of piezoelectric wafers 12 and/or their cross-sectional area and/or their thickness can be set with a constant or varying stack height. The stack height of the piezoelectric wafers 12 can for example easily be increased in that the threaded rod 4 is provided with a sufficient length for the stack height or the distance between the masses 2, 3 to be increased.

Furthermore, further system parameters such as the operating voltage, the mechanical pretensioning and the size of the masses 2, 3 or the mass distribution can also be altered in order to change or set as desired the natural frequency of the device. Examples for the influence of these parameters on the natural frequency of the device are explained in more detail in the following on the basis of FIGS. 4 to 6.

Figure 4:
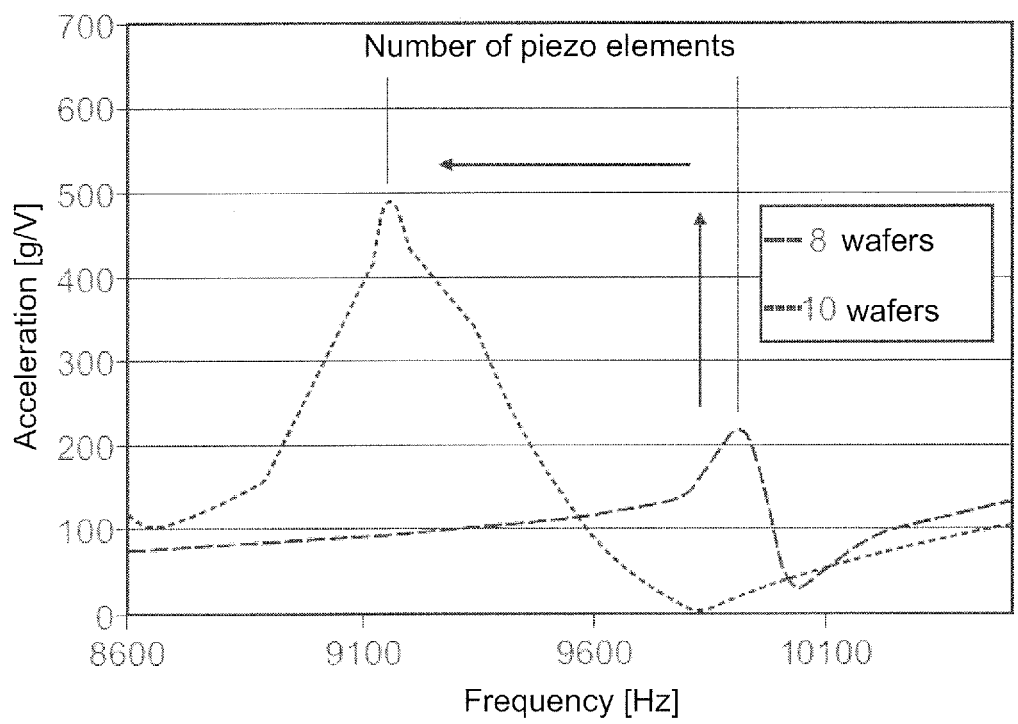
FIG. 4 shows the resonance behaviour of the device of FIG. 1 depending on the number of piezoelectric wafers.

FIG. 4 shows how the variation in the number of wafers in a piezo stack according to FIGS. 1 and 2 affects the resonance frequency. The resonance frequency was measured here on the one hand with a piezo stack having 8 wafers and on the other hand with a piezo stack having 10 wafers. Both variants were operated with the same electrical voltage, and the system response was measured with an acceleration sensor. FIG. 4 shows the recorded acceleration as a function of the frequency. It can be discerned that markedly differing resonance frequencies apply for the two design variants, while the resonance frequency decreases as the number of piezoelectric wafers increases, since the increase in the number of wafers leads to a reduction in the stiffness of the coupling system.

Figure 5A:
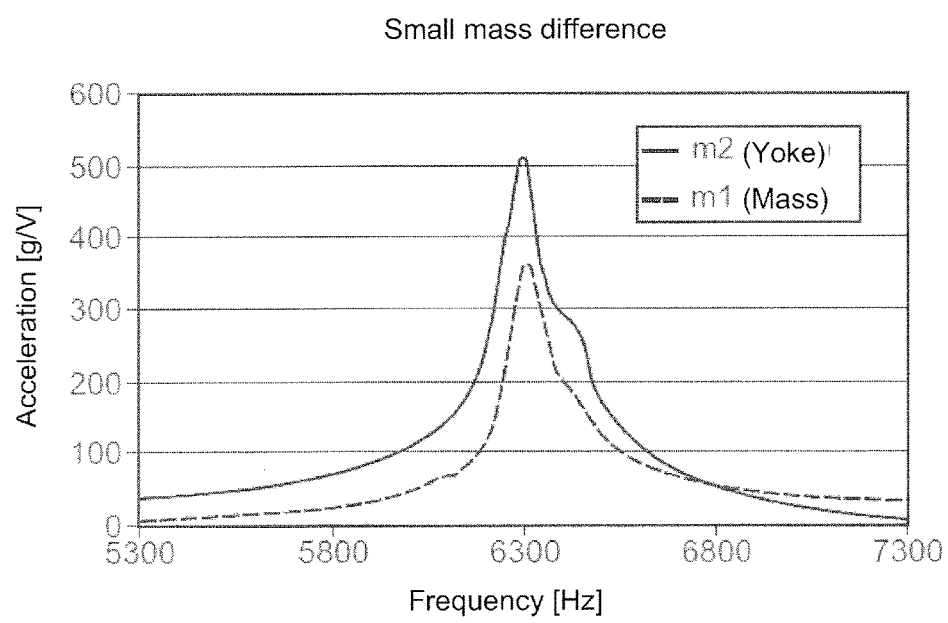
FIGS. 5A, 5B show the resonance behaviour of the device of FIG. 1 depending on the mass distribution.
Figure 5B:
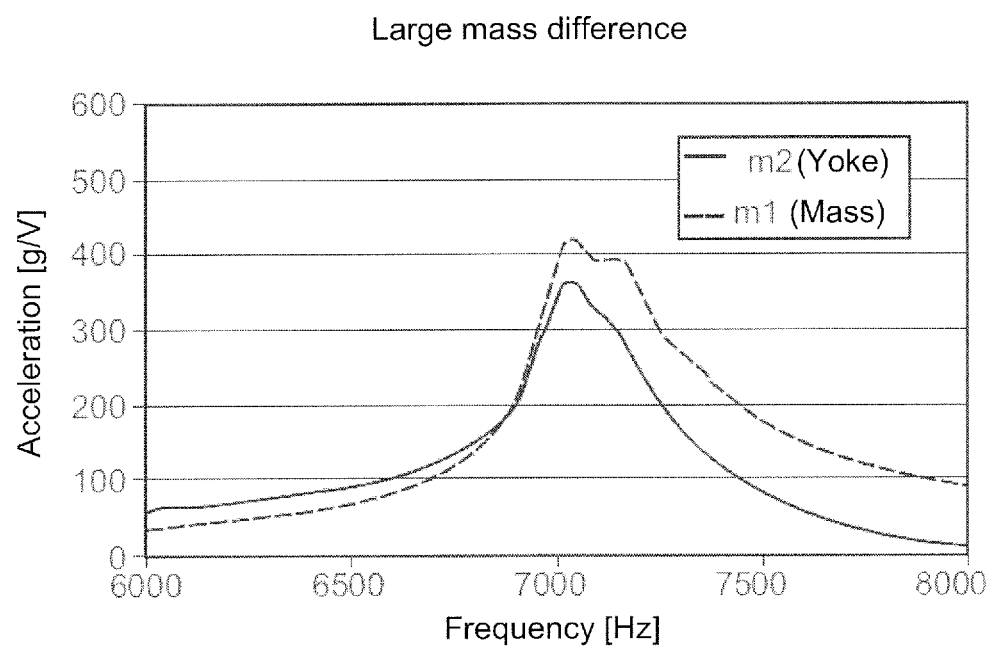

FIGS. 5A and 5B show the influence of the distribution of the masses 2, 3 on the position and course of the resonance range. The resonance behaviour was in turn measured with an acceleration sensor. In the measurement in FIG. 5A, the two masses 2, 3 ($m_2$ and $m_1$) are approximately equal in size. In the measurement in FIG. 5B, the mass 3 ($m_1$) is only about half the size of the mass of the yoke 2 ($m_2$). It can be seen that the frequency range in which resonance occurs is considerably narrower in FIG. 5A than in FIG. 5B and also has higher acceleration values. This result shows a clear dependence of the resonance frequency on the mass distribution. A large mass difference leads here in accordance with FIG. 5B to a wide frequency band in the resonance range and to a lower energy transmission. A small mass difference however leads in accordance with FIG. 5A to a small frequency band in the resonance range and to a higher energy transmission.

Figure 6:
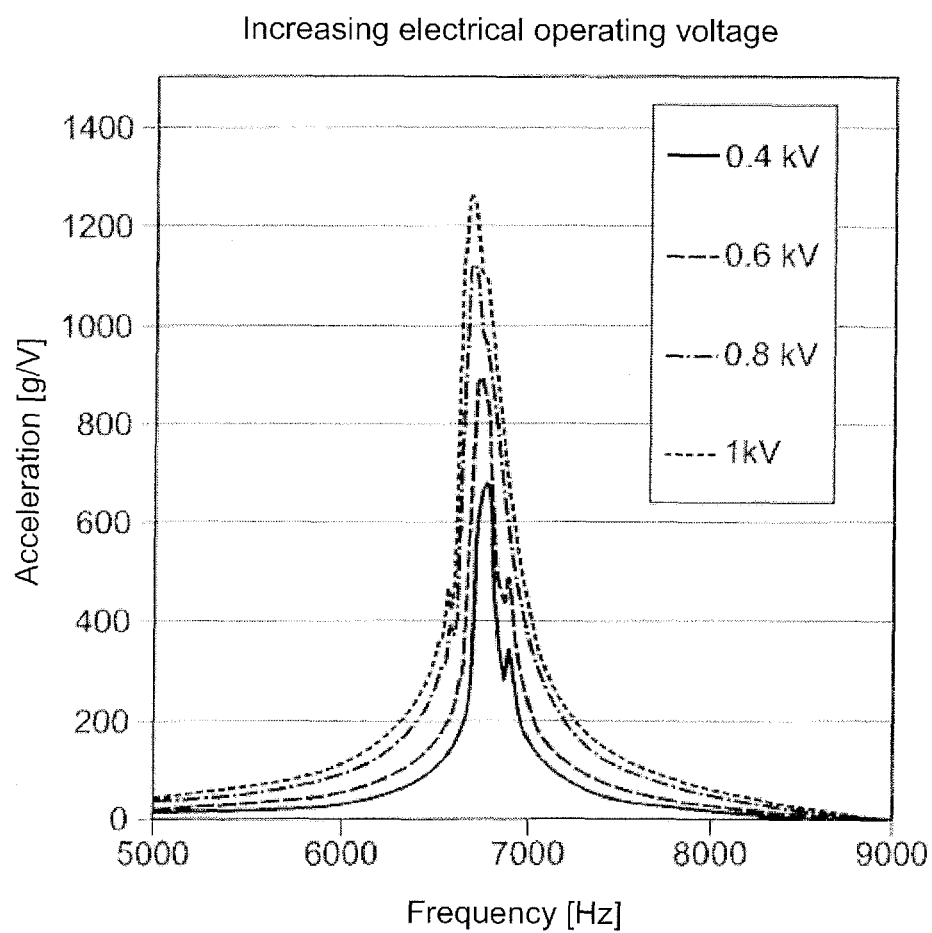
FIG. 6 shows the resonance behaviour of the device of FIG. 1 depending on the electrical operating voltage.

FIG. 6 shows the influence of the electrical operating voltage on the natural frequency of the device. The generated electrical signal is passed via an amplifier into the piezo exciter 12. In the test according to FIG. 7, the supply voltage of the system was increased step by step from 0.4 kV to 1 kV. Acceleration values were again measured and plotted against the frequency. It can be discerned here that acceleration increases proportionately with the operating voltage. At the same time, the resonance frequency decreases slightly as the operating voltage increases.

A further variation option, not shown separately, for influencing the stiffness of the piezoelectric excitation system 1 is by varying the wafer thickness of the piezoelectric wafers 12 in the device of FIGS. 1 and 2. If for example the stack height is increased by the use of thicker piezoelectric wafers 12, the stiffness of the system overall is reduced and hence the natural frequency too is reduced.

A further variation option for influencing the stiffness of the piezoelectric excitation system 1 is by selecting the cross-sectional areas of the piezoelectric wafers 12. The larger the cross-sectional area of the wafers, the greater the stiffness of the system, so that the natural frequency of the device increases with the cross-sectional area.

The setting of a desired natural frequency in a device in accordance with the invention for generating mechanical oscillations can generally be achieved by tests for setting of the various parameters. However, it is advantageous to be able to calculate analytically the resonance frequency of a device according to FIGS. 1, 2, so that for example the parameters for setting a desired resonance frequency can be suitably selected by means of a computer program. The parameters determined by the computer program then only have to be specifically set in the device. To do so, it is of course required that the calculation by the computer program correctly determines the actually occurring natural frequencies of the device.

A fatigue test on a test object is then performed in such a way that the natural frequency of the device is set to the resonance frequency of the test object (which is known) by setting the parameters established as suitable by the computer program, the test object is clamped in the yoke 2 of the device and then an AC voltage is applied to the excitation system, with this applied AC voltage having a frequency equal to the resonance frequency of the test object.

Figure 3:
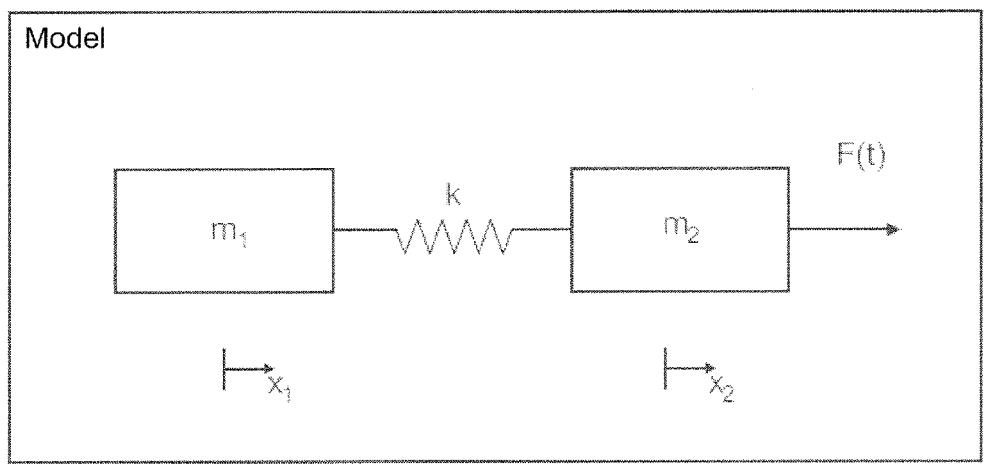
FIG. 3 shows a mathematical model of the device of FIG. 1.

For analytical calculation, the solution in accordance with the invention assumes a mathematical model that considers the device of FIGS. 1 and 2 as a two-mass oscillator. This model is shown in FIG. 3. Accordingly, the one mass has a mass $m_2$ and the other mass a mass $m_1$. The two masses $m_1$, $m_2$ are coupled to one another by a spring with the spring constant k, said spring constant k matching the stiffness constant of the piezo stack formed by the piezoelectric wafers 12. In the model considered, the two masses $m_1$, $m_2$ are each movable exclusively in the longitudinal direction $x_1$, $x_2$. Damping is disregarded. A periodic force F(t) is provided by the piezoelectric excitation.

The movement equations of the masses $m_1$, $m_2$ are each defined by the following differential equation:

$$\underline{\underline{M}}\ddot{\underline{x}} + \underline{\underline{B}}\dot{\underline{x}} - \underline{\underline{K}}\underline{x} = f(t)$$

where M indicates the mass matrix, B the damping matrix, K the stiffness matrix, x the movement direction of a mass and f the frequency. As already explained, damping is disregarded, so that B=0.

From this, the resonance frequency of the system can be calculated:

$$(f_2)_{1,2} = +\Big/-\frac{1}{2\Pi}\sqrt{\frac{k(m_1+m_2)}{m_1 m_2}},$$

where $m_1$ indicates the first mass, $m_2$ the second mass, k the stiffness constant of the overall system (i.e. the two masses $m_1$, $m_2$, of the piezoelectric excitation system and, if necessary, of further components), and $(f_2)_{1,2}$ the resonance frequency. The terms "stiffness constant" and "stiffness" are considered to be synonyms in the context of the present application.

To permit the natural frequency of the overall system to be clearly determined, the stiffness constant k must be determined according to the above equation. The stiffness constant k of the overall system is calculated in accordance with an exemplary embodiment according to the following formula:

$$k = \cfrac{1}{\sum\limits_{i=1}^{n} \cfrac{1}{k_{m,i}} + \cfrac{1}{k_{piezo}} + \cfrac{1}{k_{Electrode}}} + k_{M16}$$

Here, $k_{m,i}$ indicates the stiffness constant of the $i^{th}$ mass $m_i$, applied to the threaded rod 4, $k_{piezo}$ the stiffness constant of the piezoelectric wafers 12, $k_{elektrode}$ the stiffness constant of the electrodes 13, and $k_{M16}$ the stiffness constant of the threaded rod 4. The masses $m_i$ applied to the threaded rod 4 are in the exemplary embodiment of FIGS. 1 and 2 the centrifugal mass 3 and the additional plates 14, 15.

The stiffness and hence the resonance frequency of the overall system are therefore co-determined by the stiffness of the stack of piezoelectric wafers 12, which is settable in accordance with the invention. It is assumed here that the system is mechanically pretensioned and is at rest. The stiffness of the stack of piezoelectric wafers 12 can be calculated as follows:

$$k_{piezo} = \frac{A}{S^E_{33} * d * n}$$

Here, $k_{piezo}$ is the stiffness constant of the piezoelectric wafers, n the number of the piezoelectric wafers, d the thickness of the piezoelectric wafers, A the surface of a piezoelectric wafer, and $S^E_{33}$ the elasticity coefficient of the material of the piezoelectric wafers in their longitudinal direction (i.e. in the direction of the threaded tube 4).

The stiffness determined here includes geometric parameters of the piezoelectric wafers 12 used. The natural frequency of the overall system depends on these parameters and can be mathematically calculated by means of the stated formulas.

Figure 7:
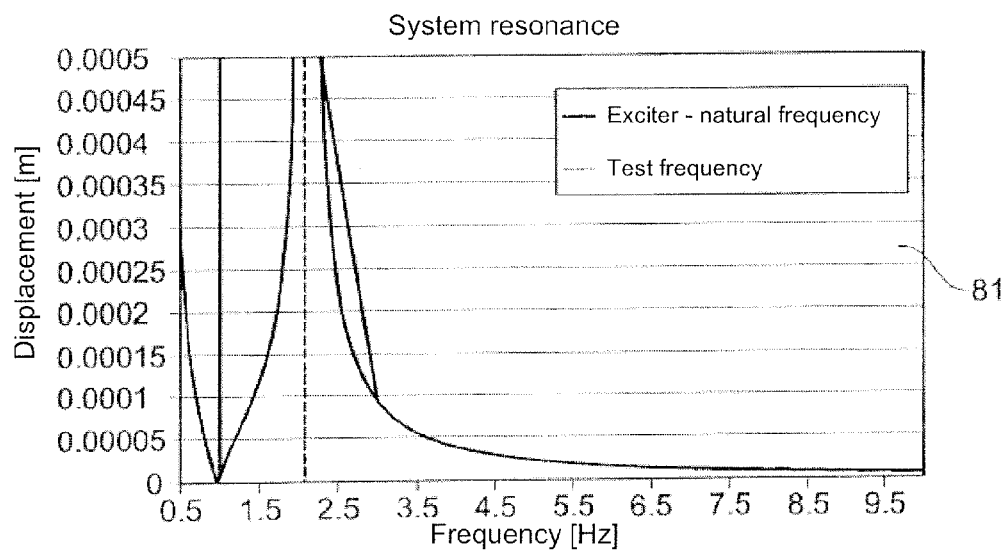
FIG. 7 shows the user interface of a computer program that calculates the resonance frequency of the device of FIG. 1 on the basis of system parameters, where an input of the system parameters necessary for calculation can be made via the user interface.

FIG. 7 shows a first exemplary embodiment of the user interface or input mask of a computer program performing a mathematical calculation of this type. On the left-hand side of the user interface, certain parameters can be set. For example, the two masses 3, 2 of the device in FIG. 1 can be entered in the fields of lines 3, 4. In the fields of lines 5 to 9 parameters of the piezoelectric wafers 12 can be set, among others thickness (line 7) and number (line 8).

The natural frequency calculated on the basis of these parameters is also graphically illustrated in a display 81. This allows easy recognition of whether the set parameters provide a desired natural frequency and, if this is not the case, resetting of the parameters to provide a desired natural frequency can be performed in a time-saving manner. It can also be provided here that the computer program submits proposals for a parameter selection leading to a desired natural frequency.

The computer program performing this calculation can additionally take into account a correction factor (cf. line 10 of FIG. 7) which accounts for the discrepancy between a resonance frequency calculated without the correction factor and a resonance frequency ascertained experimentally with a defined selection of parameters, and compensates for it.

FIG. 8 shows a second design variant of a user interface or input mask of a computer program performing a mathematical calculation of this type. The illustration in this input mask schematically represents a possible design of the piezoelectric excitation system similar to FIGS. 1 and 2, with two masses 2, 3, a threaded rod 4 and a piezoelectric excitation system having piezoelectric wafers 12, electrodes 13, additional plates 14, 15 and a spacer mass 18.

All system parameters needed can be entered into the individual fields or assigned by simply selecting them from a dropdown menu. The settable system parameters are in particular the required resonance frequency f, the outside diameter OD and the inside diameter ID of the respective masses 3, 14, 15, 18 or piezo wafers 12, the specific material, the material thickness, the mass length L the number of piezoelectric wafers 12 and the presetting of the clamped mass.

The natural frequency calculated on the basis of these parameters is numerically illustrated in a display 19. This allows easy recognition of whether the set parameters provide a desired natural frequency and, if this is not the case, resetting of the parameters to provide a desired natural frequency can be performed in a time-saving manner. It can also be provided here that the computer program submits proposals for a parameter selection leading to a desired natural frequency.

The present device and the present method lead to a considerable increase in the possibilities and the efficiency of fatigue tests performed on test objects. It is possible here to provide a desired natural frequency with only one device and in a time-saving way. The frequency spectrum that can be covered is for example in the range between 0.3 and 35 kHz. The present solution is additionally energy-saving, since the supplied energy can be transferred to the test object with a high degree of coupling due to meeting the resonance criteria.

The present invention, in its design, is not limited to the above exemplary embodiments, which are only to be understood as examples. For instance, the embodiments of the yoke 2 and the further mass 3 must be understood only as examples. The piezoelectric excitation system too can be designed in a different way and its stiffness set in a different way. Furthermore, it is pointed out that the features of the individual exemplary embodiments of the invention as described can be combined with one another in various combinations. If ranges are defined, they include all values within these ranges and all partial ranges falling within a range.

What is claimed is:

1. A device for generating mechanical oscillations for conducting a fatigue test on an engine component by exciting the engine component with a resonance frequency, comprising:
   a first mass forming a yoke to which the engine component is to be fastened,
   a second mass forming a centrifugal mass, and
   a piezoelectric excitation system mechanically coupling the first mass and the second mass to one another, with the piezoelectric excitation system having a stiffness, wherein the piezoelectric excitation system has a plurality of piezoelectric wafers forming a stack,
   wherein the stiffness of the piezoelectric excitation system is settable by setting at least one chosen from a number and a size of the piezoelectric wafers to match or approximately match a natural frequency of the device with the resonance frequency of the engine component and to then oscillate the first mass with the resonance frequency.

2. The device in accordance with claim 1, wherein the piezoelectric wafers have holes, so that the wafers can be slid or screwed onto a connecting rod.

3. The device in accordance with claim 2, wherein the first mass and the second mass are connected to one another using the connecting rod and that the piezoelectric wafers can be slid or screwed onto the connecting rod.

4. The device in accordance with claim 3, wherein the connecting rod is a threaded rod that connects the first mass and the second mass to one another.

5. The device in accordance with claim 1, wherein the piezoelectric excitation system is settable with regard to a material of the piezoelectric wafers.

6. The device in accordance with claim 1, wherein at least one chosen from the first mass and the second mass includes a plurality of fastening devices for fastening of the piezoelectric excitation system, with the piezoelectric excitation system being optionally fastenable to each of the fastening devices.

7. The device in accordance with claim 3, wherein at least one chosen from the first mass and the second mass includes a plurality of fastening devices for fastening of the piezoelectric excitation system, with the piezoelectric excitation system being optionally fastenable to each of the fastening devices and the fastening devices each having a flat mounting surface and a hole arranged in a center of the mounting surface for receiving the connecting rod.

8. A method for calculating the resonance frequency of a device for generating mechanical oscillations for a fatigue test on an engine component, comprising a first mass forming a yoke to which the engine component is to be fastened, a second mass forming a centrifugal mass and a piezoelectric excitation system, with the two masses being mechanically coupled to one another by the piezoelectric excitation system, wherein the piezoelectric excitation system has a plurality of piezoelectric wafers forming a stack, and wherein a stiffness of the piezoelectric excitation system is settable by setting at least one chosen from a number and a size of the piezoelectric wafers, with the method including the following steps:
 recording of parameters defining a stiffness of the piezoelectric excitation system,
 calculation of the resonance frequency of the device using these parameters and the first and second mass,
 wherein the calculation of the resonance frequency is based on movement equations of a two-mass oscillator, and wherein the stiffness of the piezoelectric excitation system is variably set by the at least one chosen from the number and the size of the piezoelectric wafers to achieve a natural frequency of the device which matches or approximately matches with the resonance frequency of the engine component to be tested.

9. The method in accordance with claim 8, wherein the resonance frequency is calculated according to a following formula:

$$(f_2)_{1,2} = +/- \frac{1}{2\Pi} \sqrt{\frac{k(m_1+m_2)}{m_1 m_2}},$$

where
$m_1$ indicates the first mass,
$m_2$ the second mass,
k is a stiffness constant of the overall system including the two masses $m_1$, $m_2$ and the piezoelectric excitation system, and
$(f_2)_{1,2}$ the resonance frequency.

10. The method in accordance with claim 8, wherein the parameters determining a stiffness of the piezoelectric excitation system are defined as at least one chosen from the number, the size and a material of the piezoelectric wafers of the excitation system.

11. The method in accordance with claim 8, wherein the piezoelectric excitation system includes a plurality of piezoelectric wafers and electrodes slid or screwed onto a connecting rod and forming a stack, with the stiffness of the overall system being calculated according to the following formula:

$$k = \frac{1}{\sum_{i=1}^{n} \frac{1}{k_{m,i}} + \frac{1}{k_{piezo}} + \frac{1}{k_{Electrode}}} + k_{M16}$$

where
k indicates a stiffness constant of the overall system,
$k_{m,i}$ is a stiffness constant of the respective mass slid or screwed onto the connecting rod,
$k_{piezo}$ is a stiffness constant of the piezoelectric wafers,
$k_{elektrode}$ is a stiffness constant of the electrodes, and
$k_{M16}$ is a stiffness constant of the threaded rod.

12. The method in accordance with claim 11, wherein the stiffness constant $k_{piezo}$ is calculated as follows:

$$k_{piezo} = \frac{A}{S_{33}^E * d * n}$$

where
n is the number of the piezoelectric wafers,
d is a thickness of the piezoelectric wafers,
A is a surface of a piezoelectric wafer, and
$S^E_{33}$, is an elasticity coefficient of the material of the piezoelectric wafers in their longitudinal direction.

13. The method in accordance with claim 11, wherein the stiffness constants $k_{elektrode}$ and $k_{m,i}$ are calculated according to the following formulas:

$$k_{Elektrode} = \frac{E * A_{ers}}{L * n}$$

$$k_{m,i} = \frac{E * A_{ers}}{L}$$

where
n is a number of identical electrodes,
L is a length of the masses and electrodes in the longitudinal direction,
$A_{ers}$ is a substitute cross-sectional area of a respective mass and electrode,
E is a modulus of elasticity of a respective material of the masses and electrodes, and
where a substitute cross-sectional area $A_{ers}$ is determined as follows as a function of a case distinction, depending on a geometry of the masses and electrodes:
if $D_a \leq d_w$, then:

$$A_{ers} = \frac{\pi}{4(D_a^2 - D_i^2)}$$

if $d_w \leq D_a \leq d_w + L$, then:

$$A_{ers} = \frac{\pi}{4}(d_w^2 - D_i^2) + \frac{\pi}{8}d_w(D_a - d_w)\left[\left(\sqrt[3]{\frac{L*d_w}{D_a^2}} + 1\right)^2 - 1\right]$$

if $D_a > d_w + L$ then:

$$A_{ers} = \frac{\pi}{4}(d_w^2 - D_i^2) + \frac{\pi}{8}d_w * L\left[\left(\sqrt[3]{\frac{L*d_w}{(L+d_w)^2}} + 1\right)^2 - 1\right]$$

where
$D_a$ is an outside diameter of the respective mass and electrode,
$D_i$ is an inside diameter of the respective mass and electrode,
$d_w$ is an outside diameter of a force-transmitting area of the respective mass and electrode, and
L is a length of the respective mass and electrode in the longitudinal direction.

\* \* \* \* \*